(12) United States Patent
Sun et al.

(10) Patent No.: US 8,074,739 B2
(45) Date of Patent: Dec. 13, 2011

(54) SAMPLING METHOD AND SAMPLER FOR GAS HYDRATES BY HOLE BOTTOM FREEZING

(75) Inventors: Youhong Sun, Changchun (CN); Wei Guo, Changchun (CN); Valery Konstantinovich Chistyakov, Saint-Petersburg (RU); Chen Chen, Changchun (CN); Zupei Zhang, Changchun (CN); Jun Xue, Changchun (CN)

(73) Assignee: Jilin University, Changchun, Jilin Province (CN)

( * ) Notice: Subject to any disclaimer, the term of this patent is extended or adjusted under 35 U.S.C. 154(b) by 414 days.

(21) Appl. No.: 12/402,834

(22) Filed: Mar. 12, 2009

(65) Prior Publication Data
US 2009/0229382 A1    Sep. 17, 2009

(30) Foreign Application Priority Data
Mar. 14, 2008    (CN) .......................... 2008 1 0050476

(51) Int. Cl.
*E21B 7/00*    (2006.01)
*G01N 1/22*    (2006.01)
*G01N 1/04*    (2006.01)
*G01N 1/14*    (2006.01)

(52) U.S. Cl. .................... 175/17; 73/863.11; 73/864.44; 73/864.51

(58) Field of Classification Search .................... 175/17; 73/152.11, 152.12, 152.13, 864.44
See application file for complete search history.

(56) References Cited

U.S. PATENT DOCUMENTS

| | | | | |
|---|---|---|---|---|
| 2,812,160 A | * | 11/1957 | West et al. | 175/17 |
| 4,371,045 A | * | 2/1983 | McGuire et al. | 175/17 |
| 6,378,631 B1 | * | 4/2002 | Aumann et al. | 175/249 |
| 7,748,265 B2 | * | 7/2010 | Reid et al. | 73/152.11 |

* cited by examiner

*Primary Examiner* — Hezron E Williams
*Assistant Examiner* — Nathaniel Kolb
(74) *Attorney, Agent, or Firm* — Occhiuti Rohlicek & Tsao LLP

(57) ABSTRACT

The present invention relates to a sampler for gas hydrates by hole bottom freezing, the sampler comprises a fisher, a wire-line coring mechanism and an outer barrel, and it further comprises a refrigeration portion, a low temperature control portion and a frozen insulation sample portion, which constitute an inner barrel assembly located inside the outer barrel together, wherein a refrigerant in the refrigeration portion is injected into the frozen insulation sample portion under a control of the low temperature control portion, so that a cooling medium in the frozen insulation sample portion is always kept under a predetermined temperature, and a core sample of gas hydrates is frozen at the bottom of a drill hole. The invention also relates to a sampling method using the sampler as mentioned above. In the invention, the temperature of the sample can be decreased by using an external cooling source to suppress hydrate decomposition, the critical decomposition pressure of gas hydrates can be reduced by active decreasing the temperature of the sample, and the stability of gas hydrates is maintained by a passive pressure drop. The method of the present invention need not to keep the pressure of the sample, and is simple to obtain a core sample of gas hydrates with higher fidelity.

12 Claims, 2 Drawing Sheets

SAMPLING METHOD AND SAMPLER FOR GAS HYDRATES BY HOLE BOTTOM FREEZING

CROSS-REFERENCE TO RELATED APPLICATIONS

This application claims priority to Chinese Application No. 200810050476.0, filed on Mar. 14, 2008. The content of which is hereby incorporated by reference in its entirety.

FIELD OF THE INVENTION

The present invention relates to a drilling sampler and a sampling method, especially a sampler and a sampling method for gas hydrates at the ocean bottom or land permafrost with a truth-preserving characteristic.

BACKGROUND OF THE INVENTION

With the coming of an era of high oil prices, seeking a variety of alternative energy sources has become imperative. At present, the carbon volume of gas hydrates in global seabed is two times as much as that of carbon in coal, oil and natural gas. Thus, the gas hydrate has become an important reserve energy which must be considered in the balanced development of energy strategic. The total volume of gas hydrates in South China Sea is probably half as much as that of oil and natural gas in onshore and offshore of China. Therefore, as an alternative source of energy, the development and utilization of gas hydrates have been increasingly emphasized by people in the world. Gas hydrates are mainly distributed in the seabed sediment of the ocean edge and permafrost horizon of onshore. Sample drilling is a most direct way to identifying gas hydrate, and is also the essential method to verifying the investigation achievement of other ways. So, sample drilling has great significance for the development of gas hydrates.

Gas hydrates are formed under the condition of low temperature and high pressure, such special condition needs high requirements on sample drilling. At present, the pressure-tight core barrel is a main truth-preserving core sampling tool, and its design mentality is that when the hydrate core (or core sample) has entered into the core chamber of the pressure-tight core barrel, the bottom of the core barrel is closed by a ball valve to enable the core to maintain its initial pressure, and a pressure compensation device is used to control the pressure in order to maintain it unchanged during the whole process of lifting the core from the hole bottom, and then a freezing preservation process is carried out after the core has been lifted to the ground. The heat preservation method of the core in the drill hole mainly uses thermal insulation materials to achieve passive thermal insulation. This method is used to inhibit hydrate decomposition by mechanically maintaining a constant pressure, the requirements for the strength of whole core, especially strength and sealing of the ball valve are quite high. Even if the sealing performance of the ball valve decreased slightly, the core would not be able to maintain the initial pressure, which may cause a failure of coring. When the design pressure of the sampler reaches a certain level, the materials and sealing performance of the sampler need to be improved a lot if the pressure is desired to be further increased, but it is not easy to be achieved.

SUMMARY OF THE INVENTION

In view of the above shortcomings in the prior art, an object of the present invention is to provide a sampler for gas hydrates by hole (drill hole) bottom freezing, which can decrease the critical decomposition pressure of hydrates by an active cooling process without pressure maintaining, and can realize a passive pressure drop to maintain the stability of hydrates through an external cooling source in the hole bottom to suppress hydrate decomposition by reducing the temperature of the hydrate core.

Another object of the present invention is to provide a sampling method for gas hydrates by hole bottom freezing.

The above objects of the present invention can be achieved by the following technical solution:

A refrigerant (for example, liquid nitrogen) and a cooling medium (for example, ethylene glycol) are pre-stored in a sampler, a core is frozen in the hole bottom (i.e. the bottom of a drill hole) by the cooling medium, the cooling medium is cooled by the refrigerant in a controlled manner, so that the cooling medium is always maintained under a specific temperature (for example, be lower than $-30°$ C.), in this way, the core is always under a low temperature condition throughout the process of drilling, freezing and lifting the core, thus the hydrate decomposition is suppressed.

Specially, according to one aspect of the invention, there is provided a sampler for gas hydrates by hole bottom freezing comprising a fisher, a wire-line coring mechanism and an outer barrel, wherein it further comprises a refrigeration portion, a low temperature control portion and a frozen insulation sample portion, which constitute an inner barrel assembly located inside the outer barrel together, wherein a refrigerant in the refrigeration portion is injected into the frozen insulation sample portion under a control of the low temperature control portion, so that a cooling medium in the frozen insulation sample portion is always kept under a predetermined temperature, and a core sample of gas hydrates in the frozen insulation sample portion and surrounded by the cooling medium is frozen at the bottom of a drill hole.

Preferably, the refrigeration portion comprises a upper joint and a refrigeration energy storage tank, one end of the upper joint is connected to the refrigeration energy storage tank, and the other end of the upper joint is connected to the wire-line coring mechanism.

Preferably, the low temperature control portion comprises a low-temperature control module, a switch sensor, a temperature sensor, and a temperature control electromagnetic valve, wherein the switch sensor, the temperature sensor, and the temperature control electromagnetic valve are electrically connected to the low-temperature control module respectively.

Preferably, the temperature sensor is connected to the temperature control electromagnetic valve via a temperature sensor signal line, the low-temperature control module and a temperature control signal line, the switch sensor is connected to the low-temperature control module via a switch sensor signal line, a magnet ring is embedded in the inner wall of the outer barrel, the temperature sensor and the temperature sensor signal line are surrounded by a temperature sensor protective pipe, the low temperature control module is embedded in the middle of a three-way joint and is covered by a sealing cap, which is connected to the three-way joint by thread.

Preferably, the refrigeration insulation sample portion comprises a core barrel and a cooling medium chamber surrounding the core barrel, the cooling medium chamber is connected to a refrigeration energy storage tank via a refrigerant injection pipe.

Preferably, the refrigeration insulation sample portion further comprises a cooling medium bottom cover and an insulating barrel, the lower end of the cooling medium bottom cover is connected to the lower part of the insulating barrel by thread, and the upper part of the insulating barrel is connected to a three-way joint by thread, so as to form the cooling medium chamber, a core barrel chamber is formed in the center of the cooling medium chamber, the core barrel and a split barrel are located between the core barrel chamber and the cooling medium chamber, the upper end of the core barrel is connected to the three-way joint by thread, the split barrel is lined on the inner wall of the core barrel, the upper end of the refrigerant injection pipe is connected to the refrigeration energy storage tank via a temperature control electromagnetic valve, the middle part of the refrigerant injection pipe is located in the cooling medium chamber in a spiral manner and is communicated with an exhaust valve on top of the core barrel chamber.

Preferably, a drain valve is provided in the center of the three-way joint and is communicated with an annular clearance formed between the outer barrel and the inner barrel assembly.

Preferably, the cooling medium is glycol acetal and the refrigerant is liquid nitrogen.

Preferably, the temperature of the cooling medium is always kept to be lower than −30° C.

According to another aspect of the invention, there is provided a sampling method for gas hydrates by hole bottom freezing using the sampler as mentioned above, wherein a core sample of gas hydrates is frozen at the bottom of a drill hole by a cooling medium pre-stored in the sampler, and the cooling medium is cooled by a refrigerant in a controlled manner, so that the cooling medium is always kept under a predetermined temperature.

Preferably, the method comprises the following steps:

a) filling the cooling medium into a cooling medium chamber of the sampler on the ground, covering a three-way joint on the cooling medium chamber, placing a temperature sensor and a temperature sensor signal line together with a temperature sensor protective pipe as well as a refrigerant injection pipe into the cooling medium, wherein in the sampler, a switch sensor and a switch sensor signal line is electrically connected to a low-temperature control module, a refrigeration energy storage tank is located on top of the three-way joint, the refrigerant is stored in the refrigeration energy storage tank, a refrigerant injection pipe is communicated with the refrigeration energy storage tank via a temperature control electromagnetic valve, an upper joint is covered on the refrigeration energy storage tank, after all of the above steps has been finished, putting the sampler for gas hydrates by hole bottom freezing down to the bottom of a drill hole by a wire-line coring mechanism;

b) driving a bit to work, and a core sample of gas hydrates enters into a core barrel chamber as the depth of a footage increases, when the footage reaches a predetermined depth or the core barrel chamber is completely filled with the core sample, a fisher of the sampler is putted down into the drill hole, after a hook provided on the lower end of the fisher has clamped a spearhead of the wire-line coring mechanism, the wire-line coring mechanism is brought by the fisher to lift the inner barrel assembly of the sampler a certain distance, so that the switch sensor passes through a magnetic ring embedded in the inner wall of the outer barrel of the sampler and a switch signal is generated, the switch signal is sent to the low-temperature control module via the switch sensor signal line, then the low-temperature control module starts to work;

c) after the low-temperature control module has started to work, the lifting process is stopped, and then the inner barrel assembly brings a clip spring installed at the bottom of the core barrel to move upward, and the core sample is tightly clamped and drawn to fracture through a wedge surface of a clip spring, and the cooling medium begins to freeze the core sample, and when the temperature of the cooling medium is higher than a predetermined temperature, the temperature sensor sends a signal to the low-temperature control module via the sensor signal line, then the low-temperature control module sends an instruction to the temperature-control electromagnetic valve, the refrigerant is flowed into the refrigerant injection pipe having a spiral part located in the cooling medium chamber from the refrigeration energy storage tank, so as to decrease the temperature of the cooling medium, and the refrigerant undergoing a heat exchange is transformed into a gas phase and is discharged into the core barrel chamber through an exhaust valve, the liquid in the core barrel chamber is discharged into an annular clearance formed between the outer barrel and the inner barrel assembly via a drain valve;

d) after a certain period of freezing, the hook provided on the lower end of the fisher brings the inner barrel assembly of the sampler and the core sample upward to the ground surface from the drill hole by the wire-line coring mechanism, and then the clip spring is opened, so that a split barrel and the core sample can be taken out of the core barrel.

Preferably, the predetermined temperature is −30° C.

Preferably, the certain period is 20 to 30 minutes.

The following beneficial effects can be achieved by the present invention: the shortcoming in the traditional gas hydrates sampler, which takes the core sample by a purely active pressure-tight way, is overcome, and the temperature of the gas hydrate sample in the hole bottom can be decreased by using an external cooling source to suppress hydrate decomposition. The critical decomposition pressure of gas hydrates is reduced by active decreasing the temperature of the sample, and the stability of gas hydrates is maintained by a passive pressure drop. The method of the present invention need not to keep the pressure of the sample, and is simple to obtain a core sample of gas hydrates with higher fidelity.

BRIEF DESCRIPTION OF THE DRAWINGS

Further characteristics and advantages of the present invention will become more apparent hereinafter from the following preferred embodiment of the present invention, which is shown by way of an illustrative, but not limitative, example in the accompanying drawings, wherein.

DETAILED DESCRIPTION OF THE PREFERRED EMBODIMENTS

Before the sampler for gas hydrates by hole bottom freezing of the invention is described, the structure and principle of the traditional wire-line sampler is briefly introduced hereinafter, although these contents are well known in the art.

The traditional wire-line sampler mainly comprises a fisher, a wire-line coring mechanism and an outer barrel, and it can work as follows:

1) the outer barrel and the wire-line coring mechanism are brought into a rock layer under the drilling action of a bit, and a core barrel can be filled with the core or sample by one return of drilling.

2) the fisher is connected to a steel wire and can reach the wire-line coring mechanism through the central passage of the outer barrel in the drill hole, then the wire-line coring mechanism can be lifted from the drill hole to the ground, so that a core can be obtained on the ground.

By the above process, the wire-line coring mechanism along with the core can be rapidly lifted out of the drill hole without lifting the outer barrel. The further details of the traditional wire-line sampler are common knowledge for one skilled in the art and thus will not be further discussed here.

The sampler for gas hydrates by hole bottom freezing of the invention is obtained on the basis of some improvements on the traditional wire-line sampler in consideration of the characteristics of gas hydrates.

Briefly, the sampler for gas hydrates by hole bottom freezing of the invention comprises the conventional fisher and wire-line coring mechanism in the structure, and is realized based on the characteristics of gas hydrates and a function of hole bottom freezing.

The schematic structure of the sampler for gas hydrates by hole bottom freezing according to an embodiment of the invention is described below with reference to FIG. 1.

Figure 1:
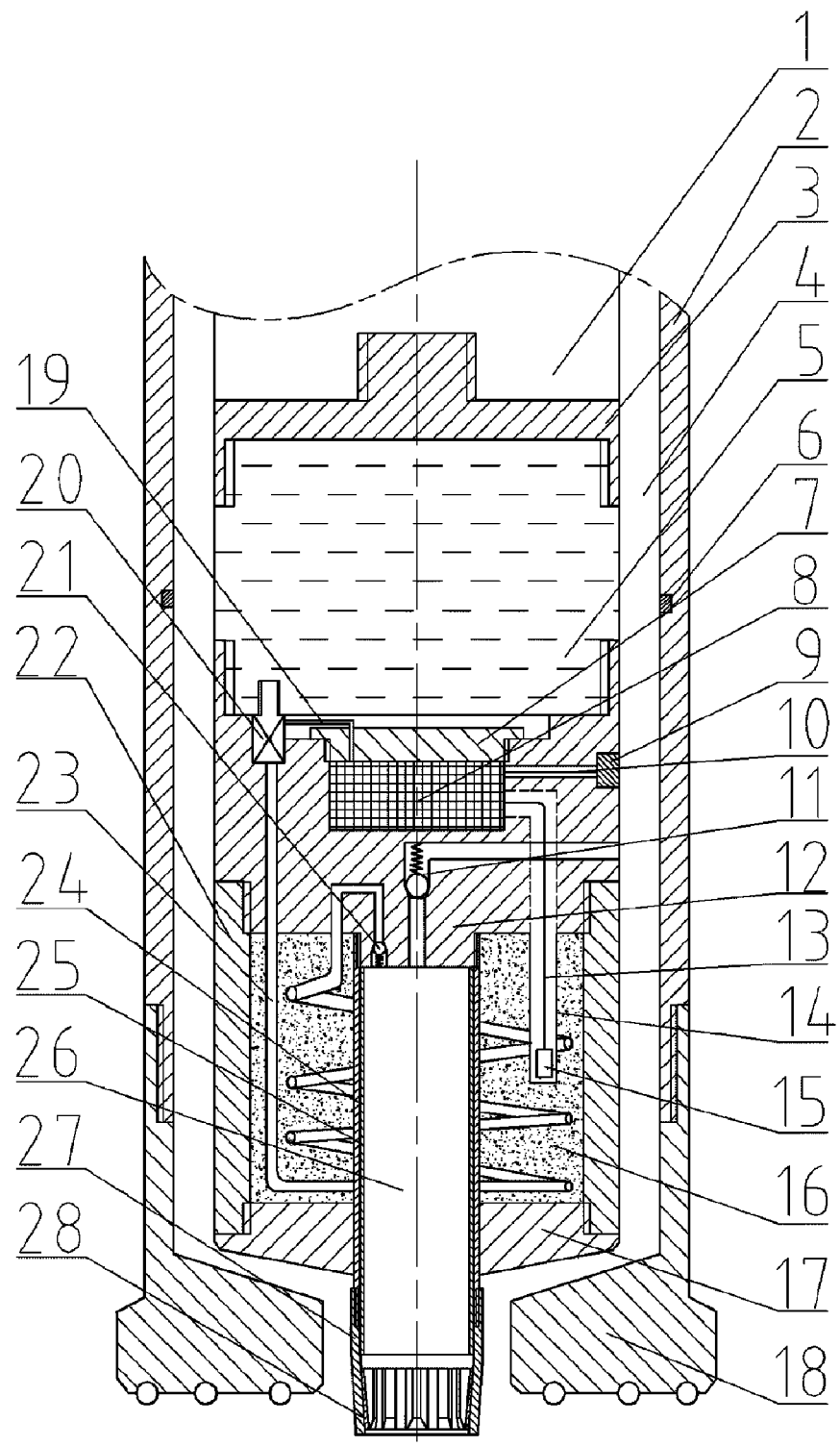
FIG. 1 schematically shows a structure of a sampler for gas hydrates by hole bottom freezing according to an embodiment of the invention.

As shown in FIG. 1, the sampler for gas hydrates by hole bottom freezing of the invention comprises a fisher (not shown), a wire-line coring mechanism 1 and an outer barrel 2, which are substantially the same as that of the traditional wire-line sampler, and it further comprises three portions, i.e. a refrigeration portion, a low-temperature control portion and a frozen insulation sample portion, the three portions constitute an inner barrel assembly as a whole.

The refrigeration portion comprises an upper joint 3 and a refrigeration energy storage tank 5, one end of the upper joint 3 is connected to the refrigeration energy storage tank 5 by thread, and the other end of the upper joint 3 is connected to the wire-line coring mechanism 1.

The low-temperature control portion comprises a low-temperature control module 8, a switch sensor 9, a temperature sensor 15 and a temperature control electromagnetic valve 20, the temperature sensor 15 is connected to the temperature control electromagnetic valve 20 via the temperature sensor signal line 13, the low-temperature control module 8 and the temperature control signal line 19, the switch sensor 9 is connected to the low-temperature control module 8 via the switch sensor signal line 10, and a magnet ring 6 is embedded in the inner wall of the outer barrel 2, by providing a temperature sensor protective pipe 14 outside of the temperature sensor 15 and the temperature sensor signal line 13, the low-temperature control module 8 is embedded in the middle of a three-way joint 12, and the low-temperature control module 8 is covered by a sealing cover 7, which is connected to the three-way joint 12 by thread.

The freezing insulation sample portion comprises a core barrel 24, a cooling medium chamber 16 surrounding the core barrel 24, a cooling medium bottom cover 17 and an insulating barrel 22, the lower part of the insulating barrel 22 is connected to the cooling medium bottom cover 17 by thread, and the upper part thereof is connected to the three-way joint 12 by thread, so that a cooling medium chamber 16 is formed, a core barrel chamber 26 is located in the center of the cooling medium chamber 16, the core barrel 24 and a split barrel 25 are arranged between the core barrel chamber 26 and the cooling medium chamber 16, the split barrel 25 is lined on the inner wall of the core barrel 24, the upper end of a refrigerant injection pipe 23 is connected to the refrigeration energy storage tank 5 through the temperature control electromagnetic valve 20. A part (middle part) of the refrigerant injection pipe 23 is arranged in the cooling medium chamber 16 in a spiral manner, and the refrigerant injection pipe 23 is communicated with an exhaust valve 21 on top of the core barrel chamber 26. A drain valve 11 and a drain pipe are provided in the center of the three-way joint 12, and communicated with an annular clearance 4 formed between the outer barrel and the inner barrel assembly as mentioned above.

Preferably, the refrigerant is liquid nitrogen and the cooling medium is ethylene glycol. Of course, other liquid well known for one skilled in the art can also be used as the refrigerant and the cooling medium according to specific applications and needs.

More specially, in the sampler for gas hydrates by hole bottom freezing of the invention, a clip spring 28 is installed on the wedge surface of a clip spring seat 27, the clip spring seat 27 is connected to the core barrel 24 by thread, the split barrel 25 is slidably engaged with the core barrel 24 located outside of the split barrel 25, the cooling medium bottom cover 17 is closely fitted with the core barrel 24 by a seal ring and is connected to the insulating barrel 22 by thread. The upper end of the insulating barrel 22 and the three-way joint 12 are connected to each other by thread, the upper end of the core barrel 24 is connected to the three-way joint 12 by thread. The cooling medium chamber 16 is located between the three-way joint 12 and the cooling medium bottom cover 17, the center of the three-channel joint 12 is provided with the drain valve 11 and the drain pipe, which communicated with the annular clearance 4. The magnet ring 6 is embedded in the inner wall of the outer barrel 2, the switch sensor 9 is installed on the three-way joint 12 and is connected to the low-temperature control module 8 through the switch sensor signal line 10, a temperature sensor protective pipe 14 is provided on one side of the three-way joint 12, the temperature sensors 15 and the temperature sensor signal line 13 are located in the temperature sensor protective pipe 14 temperature sensor protective pipe 14, the lower end of the temperature sensor protective pipe 14 is inserted into the cooling medium chamber 16, and its upper end is connected to the low-temperature control module 8, on the other side of three-way joint 12, the refrigerant injection pipe 23 is provided, the spiral middle part of which is inserted into the cooling medium chamber 16, the lower end of the refrigerant injection pipe 23 is connected to the exhaust valve 21, its upper end is connected to the temperature control electromagnetic valve 20 and communicated with the refrigeration energy storage tank 5. The temperature control electromagnetic valve 20 is connected to the low-temperature control module 8 via the temperature control signal line 19. The sealing cap 7 is connected to the three-way joint 12 by thread and it covers the low-temperature control module 8. The internal thread provided on the upper concaved end of the three-way joint 12 is engaged with the external thread provided on the lower end of the refrigeration energy storage tank 5, and the external thread provided on the upper end of the refrigeration energy storage tank 5 is engaged with the internal thread provided on the upper joint 3. The refrigeration energy storage tank 5, which can store refrigerant (in the preferred embodiment, liquid nitrogen), is located in the space between the three-way joint 12 and the upper joint 3, so as to ensure that there is no heat exchange between the refrigerant and the outside environment and the refrigerant is stored in the refrigeration energy storage tank 5 under a high-pressure condition. The outer protruding end of the upper joint 3 is connected to the wire-line coring mechanism 1 by thread. In addition, the outer barrel 2 is connected to a bit 18 by thread.

The operation, especially the low-temperature control process of the sampler for gas hydrates by hole bottom freezing of the invention is described now.

Figure 2:
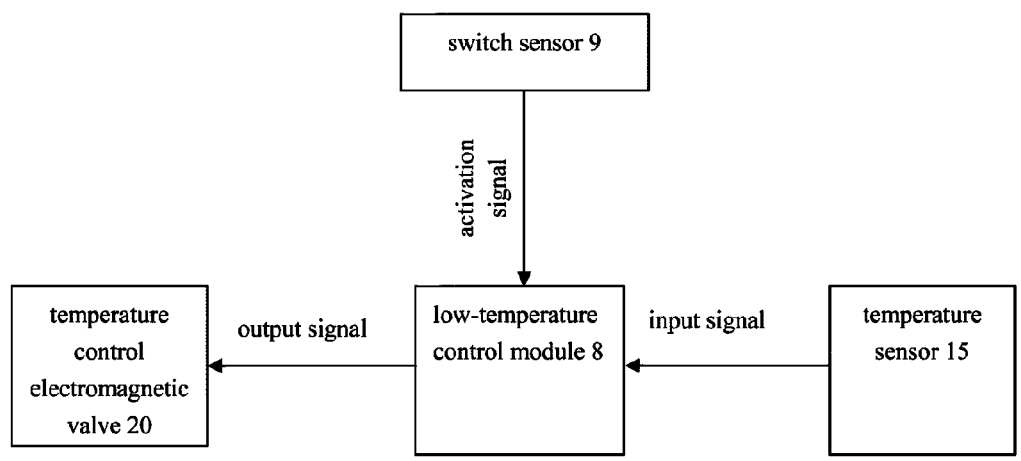
FIG. 2 shows a low-temperature control diagram of the sampler for gas hydrates by hole bottom freezing as shown in FIG. 1.

FIG. 2 shows a low-temperature control diagram of the sampler for gas hydrates by hole bottom freezing as shown in FIG. 1, the low-temperature control diagram is a general circuit for the low-temperature control module 8, wherein after the low-temperature control module 8 has received an activation signal (switch signal) from the switch sensor 9 via the sensor signal line 10, the low-temperature control module 8 begin to work. The temperature sensor 15, which timely sends temperature parameters via the temperature sensor signal line 13 to the low-temperature control module 8, measures the temperature of the cooling medium. The low-temperature control module 8 controls the solenoid valve 20 to open or close in accordance with the predetermined parameters (for example, a temperature parameter of −30° C.). For instance, when the temperature of the cooling medium is higher than −30° C., the temperature sensor 15 sends the temperature parameter in time via the temperature sensor signal line 13 to the low-temperature control module 8. At this time, the low temperature control module 8 gives an instruction to open the temperature control electromagnetic valve 20. Then, the refrigerant (liquid nitrogen in the present embodiment) is injected into the cooling medium chamber 16 through the refrigerant injection pipe 23, so as to reduce the temperature of the cooling medium.

When the temperature of the cooling medium is lower than a predetermined temperature, for example −30° C., the temperature sensor 15 sends this temperature parameter to the low-temperature control module 8 promptly via the temperature sensor signal line 13, then the low-temperature control module 8 sends a shutdown instruction to the temperature control electromagnetic valve 20 to stop the injection of the refrigerant into the cooling medium chamber 16.

During the drilling, a core sample of gas hydrates enters into the core barrel chamber 26 along with drilling of the bit 18, when the footage reaches a predetermined depth or the core barrel chamber 26 is completely filled with the core sample, the fisher is putted down into the drill hole, after a hook provided on the lower end of the fisher has clamped a spearhead of the wire-line coring mechanism 1, the wire-line coring mechanism 1 is brought by the fisher to lift the inner barrel assembly of the sampler for gas hydrates by hole bottom freezing a certain distance, so the switch sensor 9 passes through the magnetic ring 6 and a switch signal is generated, the switch signal is sent to the low-temperature control module 8 via the switch sensor signal line 10, then the low-temperature control module 8 starts to work.

After the low-temperature control module 8 has started to work, the lifting process is stopped, and a freezing process starts. At the same time, the inner barrel assembly brings the clip spring 28 installed at the bottom of the core barrel 24 to move upward, and the core sample is tightly clamped and drawn to fracture through a wedge surface of the clip spring 28. The cooling medium begins to freeze the core sample, and if the temperature of the cooling medium is higher than −30° C., the temperature sensor 15 will send a signal to the low-temperature control module 8 via the sensor signal line 13, then the low-temperature control module sends an instruction to the temperature-control electromagnetic valve 20, which starts to inject the liquid nitrogen into the cooling medium chamber 16 through the refrigerant injection pipe 23 in order to decrease the temperature of the cooling medium, and liquid nitrogen undergoing a heat exchange will be transformed into a gas phase and be discharged into the core barrel chamber 26 via the exhaust valve 21, the liquid in the core barrel chamber 26 is discharged into the annular clearance 4 via the drain valve 11. After a certain period of freezing (for example, 20-30 minutes), the hook provided on the lower end of the fisher further brings the inner barrel assembly of the sampler for gas hydrates by hole bottom freezing and the core sample upward to the ground surface from the drill hole by the wire-line coring mechanism 1, and then the clip spring 28 is opened, so that the split barrel 25 and the core sample can be taken or extracted out of the core barrel 24, thus a core extracting (coring) process without lifting the bit is realized. A latch on the top of the wire-line coring mechanism 1 is attached to the inner wall of the outer barrel 2. The wire-line coring mechanism 1 has a single acting function, which can guarantee the refrigeration portion, the low-temperature control portion and the frozen insulation sample portion will not rotate when sampling and can avoid a stir to the hydrate core.

A 9V direct current (DC) battery can be used as the power source for the switch sensor 9, which works throughout the drilling and sampling process. A 24V direct current battery can be used as the power source for the temperature control electromagnetic valve 20, the low-temperature control module 8, and the temperature sensor 15, which does not work in the drilling process.

The invention has been described in details with reference to the preferred embodiment and accompanying drawings. Obviously, the contents described above and shown in the drawings should be understood to be illustrative, rather to limit the scope of the present invention. Various modifications or changes can be made for one skilled in the art without departing from the spirit and scope of the present invention

LIST OF REFERENCE SYMBOLS 1 wire-line coring mechanism
2 outer barrel
3 upper joint
4 annular clearance
5 refrigeration energy storage tank
6 magnet ring
7 sealing cap
8 low-temperature control module
9 switch sensor
10 switch sensor signal line
11 drain valve
12 three-channel joint
13 temperature sensor signal line
14 temperature sensor protective pipe
15 temperature sensor
16 cooling medium chamber
17 cooling medium bottom cover
18 bit
19 temperature control signal line
20 temperature control electromagnetic valve
21 exhaust valve
22 insulating barrel
23 refrigerant injection pipe
24 core barrel
25 split barrel
26 core barrel chamber
27 clip spring seat
28 clip spring

What is claimed is:

1. A sampler for gas hydrates by hole bottom freezing comprising:
 a fisher, a wire-line coring mechanism,
 an outer barrel,
 an inner barrel assembly located inside the outer barrel comprising:
  a refrigeration portion,
  a low temperature control portion, and a frozen insulation sample portion, wherein a refrigerant in the refrigeration portion is injected into the frozen insulation sample portion under a control of the low temperature control portion, so that a cooling medium in the frozen insulation sample portion is always kept under a predetermined temperature, and a core sample of gas hydrates in the frozen insulation sample portion and surrounded by the cooling medium is frozen at the bottom of a drill hole, and wherein the low temperature control portion comprises a low-temperature control module, a switch sensor, a temperature sensor, and a temperature control electromagnetic valve, wherein the switch sensor, the temperature sensor, and the temperature control electromagnetic valve are electrically connected to the low-temperature control module respectively.

2. The sampler for gas hydrates by hole bottom freezing according to claim 1, wherein the refrigeration portion comprises a upper joint and a refrigeration energy storage tank, one end of the upper joint is connected to the refrigeration energy storage tank, and the other end of the upper joint is connected to the wire-line coring mechanism.

3. The sampler for gas hydrates by hole bottom freezing according to claim 1, wherein the temperature sensor is connected to the temperature control electromagnetic valve via a temperature sensor signal line, the low-temperature control module and a temperature control signal line, the switch sensor is connected to the low-temperature control module via a switch sensor signal line, a magnet ring is embedded in the inner wall of the outer barrel, the temperature sensor and the temperature sensor signal line are surrounded by a temperature sensor protective pipe, the low temperature control module is embedded in the middle of a three-way joint and is covered by a sealing cap, which is connected to the three-way joint by thread.

4. The sampler for gas hydrates by hole bottom freezing according to claim 1, wherein the refrigeration insulation sample portion comprises a core barrel and a cooling medium chamber surrounding the core barrel, the cooling medium chamber is communicated with a refrigeration energy storage tank via a refrigerant injection pipe.

5. The sampler for gas hydrates by hole bottom freezing according to claim 4, wherein the refrigeration insulation sample portion further comprises a cooling medium bottom cover and an insulating barrel, the lower end of the cooling medium bottom cover is connected to the lower part of the insulating barrel by thread, and the upper part of the insulating barrel is connected to a three-way joint by thread, so as to form the cooling medium chamber, a core barrel chamber is formed in the center of the cooling medium chamber, the core barrel and a split barrel are located between the core barrel chamber and the cooling medium chamber, the upper end of the core barrel is connected to the three-way joint by thread, the split barrel is lined on the inner wall of the core barrel, the upper end of the refrigerant injection pipe is connected to the refrigeration energy storage tank via a temperature control electromagnetic valve, the middle part of the refrigerant injection pipe is located in the cooling medium chamber in a spiral manner and is communicated with an exhaust valve on top of the core barrel chamber.

6. The sampler for gas hydrates by hole bottom freezing according to claim 5, wherein a drain valve is provided in the center of the three-way joint and is communicated with an annular clearance formed between the outer barrel and the inner barrel assembly.

7. The sampler for gas hydrates by hole bottom freezing according to claim 1, wherein the cooling medium is glycol acetal and the refrigerant is liquid nitrogen.

8. The sampler for gas hydrates by hole bottom freezing according to claim 1, wherein the temperature of the cooling medium is always kept to be lower than −30° C.

9. A sampling method for gas hydrates by hole bottom freezing using the sampler for gas hydrates by hole bottom freezing according to claim 1, wherein a core sample of gas hydrates is frozen at the bottom of a drill hole by a cooling medium pre-stored in the sampler, and the cooling medium is cooled by a refrigerant in a controlled manner, so that the cooling medium is always kept under a predetermined temperature.

10. The sampling method for gas hydrates by hole bottom freezing according to claim 9, wherein it comprises the following steps:

a) filling the cooling medium into a cooling medium chamber of the sampler on the ground, covering a three-way joint on the cooling medium chamber, placing a temperature sensor and a temperature sensor signal line together with a temperature sensor protective pipe as well as a refrigerant injection pipe into the cooling medium, wherein in the sampler, a switch sensor and a switch sensor signal line is electrically connected to a low-temperature control module, a refrigeration energy storage tank is located on top of the three-way joint, the refrigerant is stored in the refrigeration energy storage tank, a refrigerant injection pipe is communicated with the refrigeration energy storage tank via a temperature control electromagnetic valve, an upper joint is covered on the refrigeration energy storage tank, after all of the above steps have been finished, putting the sampler for gas hydrates by hole bottom freezing down to the bottom of a drill hole by a wire-line coring mechanism;

b) driving a bit to work, and a core sample of gas hydrates enters into a core barrel chamber as the depth of a footage increases, when the footage reaches a predetermined depth or the core barrel chamber is completely filled with the core sample, a fisher of the sampler is put down into the drill hole, after a hook provided on the lower end of the fisher has clamped a spearhead of the wire-line coring mechanism, the wire-line coring mechanism is brought by the fisher to lift the inner barrel assembly of the sampler a certain distance, so that the switch sensor passes through a magnetic ring embedded in the inner wall of the outer barrel of the sampler and a switch signal is generated, the switch signal is sent to the low-temperature control module via the switch sensor signal line, then the low-temperature control module starts to work;

c) after the low-temperature control module has started to work, the lifting process is stopped, and then the inner barrel assembly brings a clip spring installed at the bottom of the core barrel to move upward, and the core sample is tightly clamped and drawn to fracture through a wedge surface of a clip spring, and the cooling medium begins to freeze the core sample, and when the temperature of the cooling medium is higher than a predetermined temperature, the temperature sensor sends a signal to the low-temperature control module via the sensor signal line, then the low-temperature control module sends an instruction to the temperature-control electromagnetic valve, the refrigerant is flowed into the refrigerant injection pipe having a spiral part located in the cooling medium chamber from the refrigeration energy storage tank, so as to decrease the temperature of the cooling medium, and the refrigerant undergoing a heat exchange is transformed into a gas phase and is discharged into the core barrel chamber through an exhaust valve, the liquid in the core barrel chamber is discharged into an annular clearance formed between the outer barrel and the inner barrel assembly via a drain valve; and d) after a certain period of freezing, the hook provided on the lower end of the fisher brings the inner barrel assembly of the sampler and the core sample upward to the ground surface from the drill hole by the wire-line coring mechanism, and then the clip spring is opened, so that a split barrel and the core sample can be taken out of the core barrel.

11. The sampling method for gas hydrates by hole bottom freezing according to claim 9, wherein the predetermined temperature is −30° C.

12. The sampling method for gas hydrates by hole bottom freezing according to claim 9, wherein the certain period is 20 to 30 minutes.

\* \* \* \* \*